(«12») United States Patent
Hong

(10) Patent No.: US 6,743,806 B2
(45) Date of Patent: Jun. 1, 2004

(54) ACTIVE OXYGEN SCAVENGER

(75) Inventor: Ki Whan Hong, Busan (KR)

(73) Assignee: Otsuka Pharmaceutical Company, Limited, Tokyo-to (JP)

( * ) Notice: Subject to any disclaimer, the term of this patent is extended or adjusted under 35 U.S.C. 154(b) by 0 days.

(21) Appl. No.: 10/420,742

(22) Filed: Apr. 23, 2003

(65) Prior Publication Data

US 2004/0082608 A1 Apr. 29, 2004

Related U.S. Application Data

(62) Division of application No. 10/278,074, filed on Oct. 23, 2002, now abandoned.

(51) Int. Cl.$^7$ .............................................. A61K 31/47
(52) U.S. Cl. ..................................................... 514/312
(58) Field of Search ........................................ 514/312

(56) References Cited

U.S. PATENT DOCUMENTS 4,277,479 A     7/1981   Nishi et al. .................. 424/258

FOREIGN PATENT DOCUMENTS

JP        56-049378         5/1981

OTHER PUBLICATIONS

Shinoda–Tagawa et al., "A phosphodiesterase inhibitor, etc." CA 137:288846, dtd. 2002.
Nishi et al. IV, "Research and development, etc." CA 134:187764, dtd. 2001.
Oishi et al., "Effect of cilostazol, etc." CA 133:12525, dated 2000.
Watanabe et al., "Effect of cilostazol on, etc." CA 105:91040, dtd. 1986.
Nagai, "TNF–.alpha. formation inhibitors, etc." CA 129:76497, dtd. 1998.

Otsuka, Carbostyril derivatives, etc., CA 95:126250, dtd, 1981.
Nishi et al.., "Studies on 2–oxoquinoline, etc." CA 99:98806, dtd. 1983.
Koizumi et al., :Changes in platelet aggregability, etc. CA 132:1611050, dtd. 2000.
Lee et al., "Neuroprotective Effect of Cilostazol Against Focal Ischemic Brain Damage," The Korean Journal of Physiology & Pharmacology, vol. 5., No. 6, Supplement, P–016, (12/01).
Lee et al., "Neuroprotective Effect of Cilostazol Against Focal Ischemic Brain Damage," Program & Abstracts, The Korean Society of Pharmacology, p. 148, P 016, (11/5/01).
Jae Moon Choi et al., "Neuroprotective Effect of Cilostazol Against Focal Cerbral Ischemia via Antipoptotic Action in Rats," The Journal of Pharmacology and Experimental Therapeutics, vol. 300, No. 3, pp. 787–793, (2002).

*Primary Examiner*—James H Reamer
(74) *Attorney, Agent, or Firm*—Finnegan, Henderson, Farabow, Garrett & Dunner, L.L.P.

(57) ABSTRACT

A new active oxygen scavenger which comprises as an active ingredient a tetrazolylalkoxy-dihydrocarbostyril compound of the formula (I):

wherein R is cycloalkyl group, A is lower alkylene group, and the bond between 3- and 4-positions of the carbostyril nucleus is single bond or double bond, or a salt thereof, and an agent for the prevention or treatment of an acute cerebral infarction comprising the same active ingredient.

8 Claims, 2 Drawing Sheets

ACTIVE OXYGEN SCAVENGER

RELATED APPLICATION

This application is a divisional of application Ser. No. 10/278,074, filed Oct. 23, 2002 now abandoned which is incorporated by reference.

TECHNICAL FIELD

The present invention relates to a new active oxygen scavenger. More particularly, it relates to an active oxygen scavenger comprising as an active ingredient a tetrazolylalkoxy-dihydrocarbostyril compound of the formula (I)

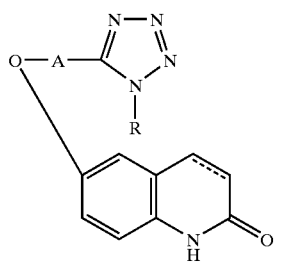

wherein R is a cycloalkyl group, A is a lower alkylene group, and the bond between 3- and 4-positions of the carbostyril nucleus means a single bond or a double bond, or a salt thereof, and an agent for the prevention or treatment of an acute cerebral infarction.

TECHNICAL BACKGROUND

Oxygen is essential for a living body in order to maintain life, for example, to keep normal energy production and metabolism. The oxygen may be changed into so-called active oxygen species such as an oxygen anion radical, a peroxyl radical, a hydroxyl radical by reactions in the energy producing system, an oxygen reaction, a reaction with ultraviolet or X-ray, etc. The active oxygen species are useful for living body, e.g. for oxygen-addition enzyme or antibacterial action of leukocytes, but on the other hand, the species promote peroxidation of unsaturated fatty acids such as oleic acid, linolenic acid, or arachidonic acid which form phospholipids in living membranes. The lipid peroxides induce generation of alkoxy radicals and hydroxyl radicals like the above active oxygen species, and attack the living membranes which results in membrane injury or inactivation of various enzymes. (cf. "TAISHA (Metabolism)" 15(10), 1978, "Special Feature of Active Oxygen") However, the living body includes various enzymes such as superoxide dimutase (SOD), catalase, glutathione peroxidase, which participate in metabolic inactivation of active oxygen species as mentioned above, and also includes vitamins such as α-tocopherol (vitamin E) which have an antioxidation activity. The living body is usually maintained in normal state by the actions of these enzymes and vitamins. However, there may happen deficiency in the biophylactic mechanism by these enzymes and vitamins or excess generation of active oxygen species which induce loss of control of the biophylactic mechanism or production and deposition of lipid peroxides. When deficiency of biophylactic mechanism occurs, peroxidation reactions will progress into chain reaction, which induce serious disorders, for example acute cerebral infarction.

SUMMARY OF THE INVENTION

The present inventors have intensively studied to develop a new medicament for scavenging active oxygen and found that the carbostyril compound of the formula (I) or a salt thereof as mentioned above, particularly 6-[4-(1-cyclohexyl-1H-tetrazol-5-yl)butoxy]-3,4-dihydrocarbostyril or a salt thereof, have an activity of scavenging active oxygen species and hence are useful as an active oxygen scavenger, and then the present invention has been accomplished.

DETAILED DESCRIPTION OF THE INVENTION

Figure 1:
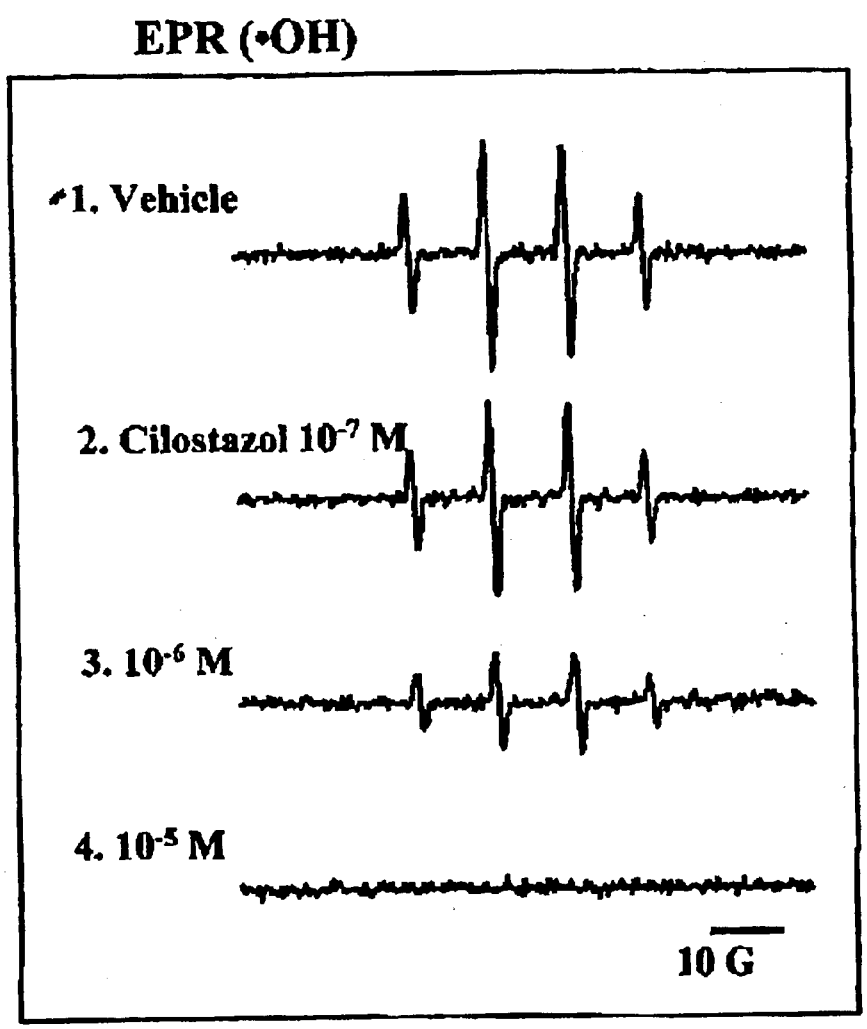
FIG. 1 shows an electron paramagnetic resonance (EPR) spectra of the spin-adduct of 5,5-dimethyl-1-pyrroline-N-oxide (DMPO) with the hydroxyl radical:
DMPO/.OH showing effect of cilostazol (tradename of 6-[4-(1-cyclohexyl-1H-tetrazol-5-yl)butoxy]-3,4-dihydrocarbostyril) on acavenging of hydroxyl radical.

The present invention provides a new active oxygen scavenger comprising as an active ingredient a tetrazolyl-alkoxy-carbostyril alkoxy-carbostyril compound of the formula (I) or a salt thereof.

The compound of the formula (I) or a salt thereof has excellent active oxygen scavenging effect and hence can inhibit the production of lipid peroxides. Thus, the active oxygen scavenger of the present invention comprising as an active ingredient the compound of the formula (I) or a salt thereof is useful for the prevention and treatment of various injuries and diseases induced by excess generation of active oxygen species, deposition of lipid peroxides or loss of biophylactic mechanism against them. Particularly, the compound of the present invention has very potent activity of scavenging hydroxyl radical having the highest toxicity to tissue among the active oxygen species and can scavenge also peroxyl radical.

More specifically, the active oxygen scavenger of the present invention is useful as a medicament for the prevention the cells in various tissues from injuries associated with ischemia, particularly reperfusion, and hence is useful for the prevention or treatment of injuries of reperfusion in the organs; the liver/renal dysfunction induced by transplantation or microcirculation dysfunction; epilepsy; acute cerebral infarction; or various disorders due to abnormal generation of active oxygen induced by any cause other than ischemia, for example arthritis.

The tetrazolylalkoxy-dihydrocarbostyril compounds of the formula (I) and processes for preparation thereof are disclosed in JP-63-20235.

In the formula (I), the "cycloalkyl group" includes cyclopropyl, cyclobutyl, cyclopentyl, cyclohexyl, cycloheptyl, cyclooctyl, etc. but preferable one is cyclohexyl. The "lower alkylene group" includes methylene, ethylene, propylene, butylene, etc. but preferable one is butylene.

Particularly preferred compound is 6-[4-(1-cyclohexyl-1H-tetrazol-5-yl)butoxy]-3,4-dihydrocarbostyril, which has been sold as a vasodilator under a tradename of cilostazol.

The compound of the formula (I) of the, present invention can be used in bulk or preferably in the form of a pharmaceutical preparation with a conventional pharmaceutical carrier or diluent. The dosage form is not limited to a specific form, but may be in any conventional dosage forms, for example, preparations for oral administration, such as tablets, capsules, granules, various liquid preparations suitable for oral administration, or preparations for parenteral administration, such as injections, suppositories. For prevention or treatment of acute cerebral infarction, it is preferable to use in the form of an injection. The dosage is not limited to a specific range but is usually in the range of 100 to 400 mg per day in adult (50 kg of body weight) which is administered once or being divided in one to several times. The active compound is preferably contained in the preparation in an amount of 50 to 100 mg per dosage unit.

The preparation for injection is usually prepared in the form of a liquid preparation, an emulsion, or a suspension, which are sterilized and further are preferably made isotonic to the blood. The preparations in the form of a liquid, emulsion or suspension are usually prepared by using conventional pharmaceutical diluents, for example, water, ethyl alcohol, propylene glycol, ethoxylated isostearyl alcohol, polyoxylated isostearyl alcohol, polyoxyethylene sorbitan fatty acid esters. These preparations may be incorporated with an isotonic agent such as sodium chloride, glucose, glycerin in an amount sufficient for making isotonic and may further incorporated with conventional solubilizers, buffers, anesthetizing agents, and optionally colorants, preservatives, fragrant materials, flavors, sweetening agents, and other medicaments.

The preparations such as tablets, capsules, liquid for oral administration may be prepared by a conventional method. The tablets may be prepared by mixing with conventional pharmaceutical carriers such as gelatin, starches, lactose, magnesium stearate, talc, gum arabic, and the like. The capsules may be prepared by mixing with inert pharmaceutical fillers or diluents and filled in a hard gelatin capsule or a soft capsule. The oral liquid preparations such as syrups or elixirs are prepared by mixing the active compound and sweetening agents (e.g. sucrose), preservatives (e.g. methylparaben, propylparaben), colorants, flavors, and the like. The preparations for parenteral administration may also be prepared by a conventional method, for example, by dissolving the compound (I) of the present invention in a sterilized aqueous carrier, preferably water or a saline solution. Preferred liquid preparation suitable for parenteral administration is prepared by dissolving about 50–100 mg of the active compound (I) in water and an organic solvent and further in a polyethylene glycol having a molecular weight of 300 to 5000, which is preferably incorporated with a lubricant such as sodium carboxymethylcellulose, methylcellulose, polyvinyl-pyrrolidone, and polyvinyl alcohol. The above liquid preparations may preferably be further incorporated with a disinfectant (e.g. benzyl, alcohol, phenol, thimerosal), a fungicide, and further optionally with an isotonic agent (e.g. sucrose, sodium chloride), a topical anesthetic, a stabilizer, a buffer, and the like. In view of keeping stability, the preparation for parenteral administration may be filled in a capsule, followed by removing the aqueous medium by a conventional lyophilizing technique, and is recovered into a liquid preparation by dissolving in an aqueous medium when used.

EXAMPLES

The present invention is illustrated by the following preparation examples and experiments of active oxygen scavenging activity of the compounds, but should not be construed to be limited thereto.

| Preparation 1 | |
|---|---|
| 6-[4-(1-Cyclohexyl-1,2,3,4-tetrazol-5-yl)butoxy]-3,4-dihydrocarbostyril | 5 g |
| Polyethyleneglycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methylparaben | 0.18 g |
| Propylparaben | 0.02 g |
| Distilled water for injection | 10.0 ml |

The above parabens, sodium metabisulfite and sodium chloride are dissolved in a half amount of the above distilled water with stirring at 80° C. The mixture is cooled to 40° C., and thereto are dissolved the active compound, and further polyethylene glycol and polyoxyethylene sorbitan monooleate. The remaining distilled water for injection is added to the mixture, sterilized by filtering with a filter paper to give the desired injection preparation.

| Preparation 2 Preparation of tablets: | |
|---|---|
| Components | Amount (g) |
| 6-[4-(1-Cyclohexyl-1,2,3,4-tetrazol-5-yl)butoxy]-3,4-dihydrocarbostyril | 100 |
| Lactose (Japanese Pharmacopeia) | 40 |
| Cornstarch (Japanese Pharmacopeia) | 40 |
| Crystalline cellulose (Japanese Pharmacopeia) | 20 |
| Hydroxypropylcellulose (Japanese Pharmacopeia) | 4 |
| Magnesium stearate (Japanese Pharmacopeia) | 2 |

The above compound of the present invention, lactose, cornstarch and crystalline cellulose are mixed well and the mixture is granulated with 5% aqueous solution of hydroxypropylcellulose, and the granulated mixture is sieved with 200 mesh screen to dry the granules carefully, and then the granules are tabletted by a conventional method to give tablets (1000 tablets).

Pharmacological Experiments

The active oxygen scavenging effects of the representative compound of the present invention: cilostazol were tested Experiment 1

Hydroxyl radical scavenging efficacy of cilostazol:

Hydroxyl radical scavenging efficacy of cilostazol was determined in air-saturated phosphate buffer (10 mM) at room temperature. The reaction was initiated by addition of a small aliquot (5 μL) of $Fe^{2+}$ solution (10 mM $FeSO_4$ in 10 mM HCl) to a buffer containing cilostazol, $H_2O_2$ (0.12 mM) and 5,5-dimethyl-1-pyrroline-N-oxide (DMPO) (1 mM). The sample was transferred quickly to flat quartz electron paramagnetic resonance (EPR) cell, and measurements were started immediately.

The EPR spectra of the spin-adduct of DMPO with the hydroxyl radical: DMPO/.OH was observed when DMPO reacted with hydroxyl radical generated by the Fenton system. The EPR spectra (.OH) are shown in the accompanying FIG. 1. Scavenging of hydroxyl radicals was confirmed by using catalase (0.510 U/ml) (data not shown).

As is seen from FIG. 1, cilostazol potently inhibited the DMPO/.OH adduct formation in a concentration-dependent manner. The signals were almost ameliorated at $10^{-5}$ M of cilostazol, suggestive of strong scavenger of hydroxyl radicals. The concentration required for inhibiting hydroxyl radical formation ($IC_{50}$) was 2.58±0.07 μM.

Experiment 2

Peroxyl radical absorbing capacity (PRAC) assay:

According to the method described by Cao et al. (Cao G, Alessio HM, Cutler RG (1993), Oxygen-radical absorbance capacity assay for antioxidants, Free Radic. Biol. Med 14: 303–311), the assay is based on production of peroxyl radicals by 2,2'-azobis(2-amidinopropane) hydrochloride (3 mM), a peroxyl radical generator, with subsequent oxidation of the reporter protein, β-phycoerythrin (16.7 nM) in 24 well plates. Into each sample well, either 20 μl of phosphate buffer or 20 μl of each concentration of cilostazol was included. After adding 2,2'-azobis(2-amidinopropane) hydrochloride, the reaction mixture was incubated at 37° C. Loss of fluorescence was measured every 5 minutes at the emission of 590 nm and excitation of 485 nm using Fluorescence Plate Reader (Bio-Tek Instruments, Inc., Winooski, USA). The PRAC value of the compound is reflected in the increase of area under curve of fluorescence versus time. Trolox was used as a reference for PRAC assay. The fluorescence just prior to addition of the 2,2'-azobis(2-amidinopropane) hydrochloride was estimated as the 100% value for that sample. The PRAC values were calculated by the following equation:

$$PRAC = \frac{[\text{Area of compound} - \text{Area of blank}]}{[\text{Area of 1 μM trolox} - \text{Area of blank}]}$$

where 1 PRAC unit is the value of 1 μM of trolox.

Figure 2:
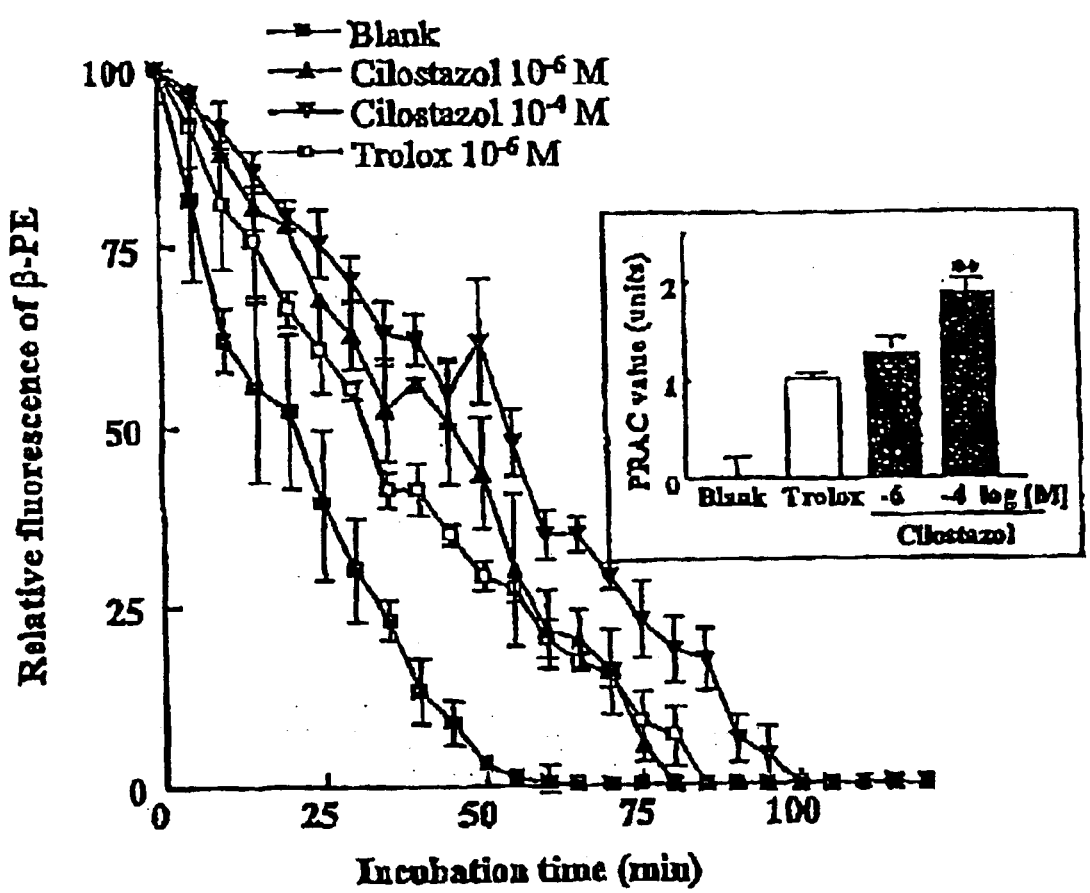
FIG. 2 shows the time-dependent decrease of β-phycoerythrin fluorescence in the absence (blank) and the presence of different concentrations of cilostazol, which shows peroxyradical absorbing capacity of cilostazol.

The time-dependent decrease of β-phycoerythrin fluorescence in the absence (blank) and the presence of different concentrations of cilostazol is shown, in the accompanying FIG. 2. As is shown in FIG. 2, the β-phycoerythrin is characterized by its ability toil rapidly lose its fluorescence when exposed to a source, of free radicals. The decrease in the β-phycoerythrin fluorescense showed a delay time dependency, on the concentration of the antioxidants for time length of 125 minutes. In the presence of $10^{-6\ and}\ 10^{-4}$ M of cilostazol, there was a right shift of the extinction curve, suggestive of its scavenging effect. The PRAC values (unit) calculated for cilostazol ($10^{-6}$ and $10^{-4}$ M) were 1.325 and 1.938, respectively.

What is claimed is:

1. A method of scavenging an active oxygen, which comprises administering to a subject in need thereof an effective amount of a tetrazolylalkoxy-dihydrocarbostyril compound of the formula (I)

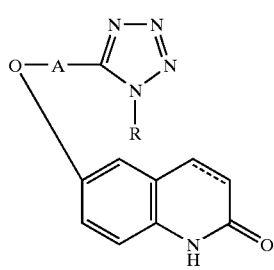

(I)

wherein R is a cycloalkyl group, A is a lower alkylene group, and the bond between 3- and 4-positions of the carbostyril nucleus is a single bond or a double bond, or a pharmaceutically acceptable salt of said compound.

2. The method according to claim 1, wherein the tetrazolylalkoxy-dihydrocarbostyril compound (I) is 6-[4-(1-cyclohexyl-1H-tetrazol-5-yl)butoxy]-3,4-dihydrocarbostyril or a pharmaceutically acceptable salt thereof.

3. A method of scavenging a hydroxyl radical, which comprises administering to a subject in need thereof an effective amount of a tetrazolylalkoxy-dihydrocarbostyril compound

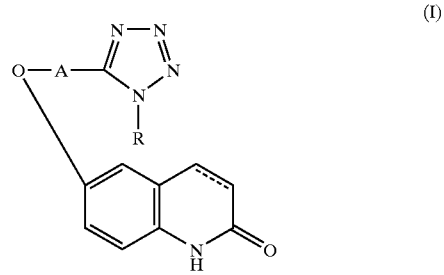

(I)

wherein R is a cycloalkyl group, A is a lower alkylene group, and the bond between 3- and 4-positions of the carbostyril nucleus is a single bond or a double bond, or a pharmaceutically acceptable salt of said compound.

4. The method according to claim 3, wherein the tetrazolylalkoxy-dihydrocarbostyril compound (I) is 6-[4-(1-cyclohexyl-1H-tetrazol-5-yl)butoxy]3,4-dihydrocarbostyril or a pharmaceutically acceptable salt thereof.

5. A method for the treatment of injuries and diseases induced by excess generation of active oxygen species, which comprises administering to a subject in need of such treatment an effective amount of a tetrazolylalkoxy-dihydrocarbostyril compound

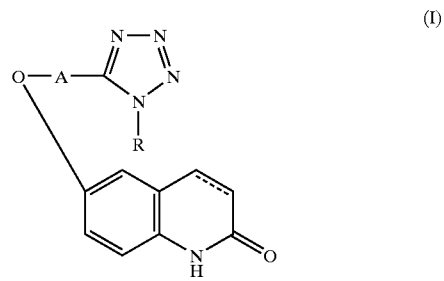

(I)

wherein R is a cycloalkyl group, A is a lower alkylene group, and the bond between 3- and 4-positions of the carbostyril nucleus is a single bond or a double bond, or a pharmaceutically acceptable salt of said compound.

6. The method according to claim 5, wherein the tetrazolylalkoxy-dihydrocarbostyril compound (I) is 6-[4-(1-cyclohexyl-1H-tetrazol-5-yl)butoxy]-3,4-dihydrocarbostyril or a pharmaceutically acceptable salt thereof.

7. A method for the treatment of injuries of reperfusion in the organs, the liver or renal dysfunction induced by transplantation or microcirculation dysfunction, epilepsy, acute cerebral infarction, or disorders due to abnormal generation of active oxygen induced by any cause other than ischemia, which comprises administering to a subject in need of such treatment an effective amount of a tetrazolylalkoxy-dihydrocarbostyril compound

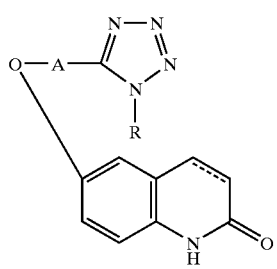

(I)

wherein R is a cycloalkyl group, A is a lower alkylene group, and the bond between 3- and 4-positions of the carbostyril nucleus is a single bond or a double bond, or a pharmaceutically acceptable salt of said compound.

8. The method according to claim 7, wherein the tetrazolylalkoxy-dihydrocarbostyril compound (I) is 6-[4-(1-cyclohexyl-1H-tetrazol-5-yl)butoxy]-3,4-dihydrocarbostyril or a pharmaceutically acceptable salt thereof.

* * * * *

(12) EX PARTE REEXAMINATION CERTIFICATE (6479th)
United States Patent
Hong

(10) Number: US 6,743,806 C1
(45) Certificate Issued: Oct. 14, 2008

(54) ACTIVE OXYGEN SCAVENGER

(75) Inventor: Ki Whan Hong, Busan (KR)

(73) Assignee: Otsuka Pharmaceutical Company, Limited, Chiyoda-Ku, Tokyo-to (JP)

Reexamination Request:
No. 90/007,573, Jun. 3, 2005

Reexamination Certificate for:
Patent No.: 6,743,806
Issued: Jun. 1, 2004
Appl. No.: 10/420,742
Filed: Apr. 23, 2003

Related U.S. Application Data

(62) Division of application No. 10/278,074, filed on Oct. 23, 2002, now abandoned.

(51) Int. Cl.
*A61K 31/4709* (2006.01)
*C07D 401/12* (2006.01)
*C07D 401/00* (2006.01)

(52) U.S. Cl. ...................................................... 514/312
(58) Field of Classification Search .................. None
See application file for complete search history.

(56) References Cited

PUBLICATIONS

Hirsch et al. Curr Treat Options Cardiovasc Med. 2001 Jun., 3(3):167–180.*
Mugge A. Zeitschrift fur Kardiologie, 1998, 87(11): 851–64.*
Hakim et al. Journal of Trauma: Injury, Infection and Critical Care, 1999, 46(5):869–872.*
Kim et al. The Journal of Pharmacology and Experimental Therapeutics. 2002, Feb., 300(2):709–714.*
Takei, et al., Role of Cyclic Adenosine Monophosphate in Reducing Superoxide Anion Generation in Guinea Pig Alveolar Macrophages, *Pharmacology*, 1998, vol. 57 pp. 1–7.
Watanabe, et al., Effect of Cilostazol on Experimental Cerebral Infarction in Rabbits, *Arzneimittel–Forschung/Drug Research*, 1986, 36(7):1022–24.
Tsutsui et al., Ameliorative Effect of Cilostazol on Cerebral Ischemia and Cerebral Embolization, *The Japanese Journal of Pharmacology*, Supp. 1989, vol. 49, 232P, P–183.
Tanaka, et al., Effects of a Selective Inhibitor of Cyclic AMP Phosphodiesterase on the Pial Microcirculation in Feline Cerebral Ischemia, *Stroke*, 1989, vol. 20(5) pp. 668–673.

* cited by examiner

*Primary Examiner*—Evelyn Huang

(57) ABSTRACT

A new active oxygen scavenger which comprises as an active ingredient a tetrazolylalkoxy-dihydrocarbostyril compound of the formula (I):

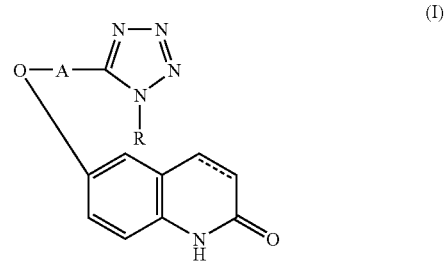

wherein R is cycloalkyl group, A is lower alkylene group, and the bond between 3- and 4-positions of the carbostyril nucleus is single bond or double bond, or a salt thereof, and an agent for the prevention or treatment of an acute cerebral infarction comprising the same active ingredient.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–8 are cancelled.

* * * * *